United States Patent
West et al.

(10) Patent No.: US 6,645,517 B2
(45) Date of Patent: Nov. 11, 2003

(54) TEMPERATURE-SENSITIVE POLYMER/ NANOSHELL COMPOSITES FOR PHOTOTHERMALLY MODULATED DRUG DELIVERY

(75) Inventors: Jennifer L. West, Pearland, TX (US); Scott R. Sershen, Houston, TX (US); Nancy J. Halas, Houston, TX (US); Steven J. Oldenburg, San Diego, CA (US); Richard D. Averitt, Los Alamos, NM (US)

(73) Assignee: William Marsh Rice University, Houston, TX (US)

( * ) Notice: Subject to any disclaimer, the term of this patent is extended or adjusted under 35 U.S.C. 154(b) by 0 days.

(21) Appl. No.: 10/164,269

(22) Filed: Jun. 5, 2002

(65) Prior Publication Data

US 2002/0169235 A1 Nov. 14, 2002

Related U.S. Application Data

(60) Division of application No. 09/616,127, filed on Jul. 14, 2000, now Pat. No. 6,428,811, which is a continuation-in-part of application No. 09/038,377, filed on Mar. 11, 1998, now Pat. No. 6,344,272.
(60) Provisional application No. 60/144,296, filed on Jul. 16, 1999.

(51) Int. Cl.$^7$ .................................................. A61F 13/00
(52) U.S. Cl. ...................................................... 424/422
(58) Field of Search ............................... 424/490, 497; 428/403

(56) References Cited

U.S. PATENT DOCUMENTS

| 3,856,398 A | 12/1974 | Taylor ........................ 355/64 |
| 4,099,854 A | 7/1978 | Decker et al. ................ 350/312 |
| 4,123,396 A | 10/1978 | Rembaum et al. ............. 526/24 |

(List continued on next page.)

FOREIGN PATENT DOCUMENTS

| WO | WO90/11890 | 10/1990 |
| WO | WO97/40181 | 10/1997 |
| WO | WO98/04740 | 2/1998 |
| WO | WO98/33070 | 7/1998 |

OTHER PUBLICATIONS

Birnboim, Meyer H., *Nonlinear Optical Properties of Structured Nanoparticle Composites*, Mat. Res. Soc. Symp. Proc. vol. 164, 1990, pp. 277–282.

(List continued on next page.)

Primary Examiner—Carlos A. Azpuru
(74) Attorney, Agent, or Firm—Conley & Rose, P.C.

(57) ABSTRACT

A thermally sensitive polymer-particle composite that absorbs electromagnetic radiation, and uses the absorbed energy to trigger the delivery of a chemical is disclosed. Metal nanoshells are nanoparticulate materials that are suitable for use in the present composites and can be made according to a process that includes optically tuning or tailoring their maximum optical absorption to any desired wavelength primarily by altering the ratio of the core diameter to the shell thickness. Preferred nanoshells are selected that strongly absorb light in the near-infrared and thus produce heat. These nanoshells are combined with a temperature-sensitive material to provide an implantable or injectable material for modulated drug delivery via external exposure to near-IR light. This invention provides a means to improve the quality of life for persons requiring multiple injections of a drug, such as diabetes mellitus patients.

20 Claims, 6 Drawing Sheets

U.S. PATENT DOCUMENTS

| | | | |
|---|---|---|---|
| 4,313,734 A | 2/1982 | Leuvering | 23/230 |
| 4,416,998 A | 11/1983 | Adams et al. | 436/86 |
| 4,452,773 A | 6/1984 | Molday | 424/1.1 |
| 4,481,091 A | 11/1984 | Brus et al. | 204/157.1 |
| 4,624,923 A | 11/1986 | Margel | 435/176 |
| 4,877,647 A | 10/1989 | Klabunde | 427/123 |
| 4,979,821 A | 12/1990 | Schutt et al. | 356/246 |
| 5,023,139 A | 6/1991 | Birnboim et al. | 428/402 |
| 5,025,147 A | 6/1991 | Dürig et al. | 250/216 |
| 5,213,788 A | 5/1993 | Ranney | 424/9 |
| 5,213,895 A | 5/1993 | Hirai et al. | 428/403 |
| 5,249,077 A | 9/1993 | Laronga et al. | 359/385 |
| 5,266,498 A | 11/1993 | Tarcha et al. | 436/525 |
| 5,322,798 A | 6/1994 | Sadowski | 436/113 |
| 5,338,353 A | 8/1994 | Uchino et al. | 106/426 |
| 5,376,556 A | 12/1994 | Tarcha et al. | 436/525 |
| 5,427,767 A | 6/1995 | Kresse et al. | 424/9 |
| 5,445,972 A | 8/1995 | Tarcha et al. | 436/544 |
| 5,451,525 A | 9/1995 | Shenkin et al. | 436/63 |
| 5,479,024 A | 12/1995 | Hillner et al. | 250/458.1 |
| 5,501,949 A | 3/1996 | Marshall | 435/5 |
| 5,521,289 A | 5/1996 | Hainfeld et al. | 530/391.5 |
| 5,545,250 A | 8/1996 | Bergmann et al. | 75/252 |
| 5,552,086 A | 9/1996 | Siiman et al. | 252/408.1 |
| 5,567,628 A | 10/1996 | Tarcha et al. | 436/525 |
| 5,599,668 A | 2/1997 | Stimpson et al. | 435/6 |
| 5,779,976 A | 7/1998 | Leland et al. | 422/52 |
| 5,817,462 A | 10/1998 | Garini et al. | 435/6 |
| 5,938,617 A | 8/1999 | Vo-Dinh | 600/476 |
| 5,945,293 A | 8/1999 | Siiman et al. | 435/7.24 |
| 5,962,218 A | 10/1999 | Leland et al. | 435/6 |
| 5,990,479 A | 11/1999 | Weiss et al. | 250/307 |
| 5,993,374 A | 11/1999 | Kick | 600/8 |
| 6,068,857 A | 5/2000 | Weitschies et al. | 424/489 |
| 6,078,782 A | 6/2000 | Leland et al. | 250/307 |
| 6,180,415 B1 | 1/2001 | Schultz et al. | 436/518 |

OTHER PUBLICATIONS

Nedelijkovic, Jovan; *Observation of Plasmon–Enhanced Optical Extinction in Silver–Coated Silver Bromide Nanoparticles*, American Institute of Physics, Jun. 3, 1991, pp. 2461–2463.

Oldenburg, S.J.; *Nanoengineering of Optical Resonances*, Chemical Physics Letters 288 (1988), pp. 243–247.

Westcott, Sarah; *Formation and Adsorption of Clusters of Gold Nanoparticles onto Functionalized Silica Nanoparticle Surfaces*, Langmuir, 1998, vol. 14, No. 19, pp. 5396–5401.

Zhou, H.S.; *Controlled Synthesis and Quantum–Size Effect in Gold–Coated Nanoparticles*, American Physical Society, 1994, vol. 50, No. 16, pp. 12 052–12 056.

Zhou, H.S., *Synthesis and Optical Properties of Coated Nanoparticle Composites*, Journal of Luminescence, 70, 1996, pp. 21–34.

R. D. Averitt, et al; *Optical Properties and Growth Kinetics of Au coated au_2S Nanoshells*; Web Publication ; Jan. 10, 1997; (1 p.).

S. J. Oldenburg, et al; *Self–assembled Metal Shell Nanoparticles*; Web Publication; Jan. 10, 1997; (1 p.).

J. I. Steinfeld; *An Introduction to Modern Molecular Spectroscopy*; The MIT Press; Second Edition; Copyright©1974 and 1985; (8 p.).

P. F. Bernath; *Spectra of Atoms and Molecules*; Oxford University Press 1995; (8 p.).

R. D. Averitt, et al; *Ultrafast Electron Dynamics in Gold Nanoshells*; The American Physical Society vol. 58, No. 16; 1998; (4 p.).

J. W. Haus, et al; *Nonlinear–Optical Properties of Conductive Spheroidal Particle Composites*; Optical Society of America, vol. 6, No. 4, Apr. 1989; (pp. 797–807).

D. Stroud, et al; *Decoupling Approximation for the Nonlinear–Optical Response of Composite Media*; Optical Society of America, vol. 6, No. 4, Apr. 1989; (pp. 778–786).

A. E. Neeves, et al; *Composite Structures for the Enhancement of Nonlinear–Optical Susceptibility*; Optical Society of America; vol. 6, No. 4, Apr. 1989; (pp. 787–796).

P. Barnickel, et al; *Silver Coated Latex Spheres*; Molecular Physics, 1989, vol. 67, No. 6; (pp. 1355–1372).

R. D. Averitt, et al; *Plasmon Resonance Shifts of Au–Coated $Au_2S$ Nanoshells: Insight into Multicomponent Nanoparticle Growth*; Physical Review Letters, Jun. 2, 1997, vol. 78, No. 22; (pp. 4217–4220).

D. Sarkar, et al; *General Vector Basis Function Solution of Maxwell's Equations*; Physical Review, vol. 56, No. 1, Jul. 1997; (pp. 1102–1112).

J. Oldenburg, et al, *Surface Enhanced Raman Scattering in the Near Infrared using Metal Nanoshell Substrates*, Journal of the American Chemical Society, submitted (1998).

T.E. Rohr, et al., *Immunoassay Employing Surface–Enhanced Raman Spectroscopy*, Analytical Biochemistry 182, 388–398 (1989).

Luis M. Liz–Marzan, Michael Giersig, and Paul Mulvaney, "Synthesis of Nanosized Gold—Silica Core—Shell Particles," Langmuir 1996, 12, 4329–4335.

S.J. Oldenburg, J.B. Jackson, S.L. Westcott, and N.J. Halas, "Infrared Extinction Properties Of Gold Nanoshells", Applied Physics Letters, vol. 75, No. 19, pp. 2897–2899 (1999).

Gregorakis, Alkibiades K. et al.; *Prostate–Specific Membrane Antigen: Current and Future Utility*; Seminars in Urologic Oncology, vol. 16, No. 1; Feb. 1998; (pp.2–12.

Ozzello, L., et al; *Conjugation of Interferon Alpha to a Humanized Monoclonal Antibody (HuBrE–3v1) Enhances the Selective Localization and Antitumor Effects of Interferon in Breast Cancer Xenografts*; Breast Cancer Research and Treatment 48: 1998; (pp. 135–147).

Bange, Johannes, ete al.; *Molecular Targets for Breast Cancer Therapy and Prevention*;; Nature Medicine; vol. 7, No. 5, May 2001; (pp. 548–552).

Vriesendorp, Huib M., et al; *Radiolabeled Immunoglobulin Therapy in Patients with Hodgkin's Disease*; Cancer Biotherapy & Radiopharmaceuticals; vol. 15, No. 5, 2000; (pp. 431–445).

Chance, B., et al.; *Highly Sensitive Object Location in Tissue Models with Linear In–Phase and Anti–Phase Multi–Element Optical Arrays in One and Two Dimensions*; Proc. Natl. Acad. Sci. USA, vol. 90, Apr. 1993; (pp. 3423–3427).

Chen, Wei R. et al; *Laser–Photosensitizer Assisted Immunotherapy: a Novel Modality for Cancer Treatment*; Cancer Letters 115 (1997) (pp. 25–30).

Chen, Wei R., et al; *Photothermal Effects on Murine Mammary Tumors Using Indocyanine Green and an 808–nm Diode Laser: An in Vivo Efficacy Study*; Cancer Letters 98 (1996) (pp. 169–173).

Chen, Wei R., et al; *Chromophore–Ehanced in Vivo tumor Cell Destruction Using an 808–nm Diode Laser*; ; Cancer Letters 94 (1996) (pp. 125–131).

Chen, Wei R., et al; *Chromophore–Enhanced laser–tumor Tissue Photothermal Interaction Using an 808–nm Diode Laser*; Cancer Letters 88 (1995) (pp. 15–19).

Jeong, B., et al; *New Biodegradable Polymers for Injectable Drug Delivery Systems*; Journal of Controlled Release 62 (1999) (pp. 109–114).

Vrouenraets, Maarten B., et al; *Development of meta–Tetrahydroxyphenylchlorin–Monocional Antibody Conjugates for Photoimmunotherapy*; Cancer Research 59; Apr. 1, 1999; (pp. 1505–1513).

Priest, John H., et al.; *Lower Critical Solution Temperatures of Aqueous Copolymers of N–Isopropylacrylamide and Other N–Substituted Acrylamides*; Chapter 18; Amer. Chem. Soc. 1987; (pp. 255–264).

Dong, Liang C., et al; *Thermally Reversible Hydrogels*; Chapter 16; Amer. Chem. Soc. 1987; (pp. 236–244).

Eriksson, Cecilia, et al.; *The Initial Reactions of Graphite and Gold with Blood*; John Wiley & Sons, Inc.; 1997; (pp. 130–136).

Weissleder, Ralph, et al.; *In Vivo Imaging of Tumors with Protease–Activated Near–Infrared Fluorescent Probes*; Nature Biotechnology; vol. 17, Apr. 1999; (pp. 375–378).

Dong, Liang C., et al; *Thermally Reversible Hydrogels: III. Immobilization of Enzymes for Feedback Reaction Control*; Elsevier Science Publishers B.V.; 1986; (pp. 223–227).

Yoshida, Ryo, et al.; *Modulating the Phase Transition Temperature and Thermosensitivity in N–Isopropylacrylamide Copolymer Gels*; J. Biomater. Sci. Polymer Edn., vol. 6, No. 6, 1994; (pp. 585–598).

Hoffman, Allan S., et al.; *Thermally Reversible Hydrogels: II. Delivery and Selective Removal of Substances from Aqueous Solutions*; Elsevier Science Publishers B.V.; 1986; (pp. 213–222).

Fisher, Anita M.R., et al.; *Clinical and Preclinical Photodynamic Therapy*; Lasers in Surgery and Medicine 17:2–31 (1995) Wiley–Liss, Inc.; (pp. 1–31).

TEMPERATURE-SENSITIVE POLYMER/ NANOSHELL COMPOSITES FOR PHOTOTHERMALLY MODULATED DRUG DELIVERY

CROSS-REFERENCE TO RELATED APPLICATIONS

This application is a DIV of Ser. No. 09/616,127 filed Jul. 14, 2000 U.S. Pat. No. 6,428,811 which is a continuation-in-part of U.S. patent application Ser. No. 09/038,377 filed Mar. 11, 1998, and also claims the benefit of U.S. Provisional Application No. 60/144,296 filed Jul. 16, 1999. The disclosures of those applications are incorporated herein by reference.

STATEMENT REGARDING FEDERALLY SPONSORED RESEARCH OR DEVELOPMENT

This invention was made with government support under Grant No. N00014-97-1-0217 awarded by the Office of Naval Research. The United States government has certain rights in the invention.

BACKGROUND OF THE INVENTION

1. Field of the Invention

The present invention generally relates to chemical delivery by controlled release from an implanted device or medium. More particularly, the invention relates to composite materials containing a temperature-sensitive polymer, a drug, and light-absorbing particles, and to methods of photothermally modulating drug release.

2. Description of Related Art

Modulated drug delivery allows the release profiles of therapeutic agents to be manipulated to match the physiological requirements of the patient. This type of controlled delivery system is useful for treating diseases that affect the homeostatic functions of the body, such as diabetes mellitus. Insulin therapy for diabetes requires a low baseline release of the drug, with peaks after the ingestion of food (O. B. Crofford *Ann. Rev. Med.* 46:267–279 (1995); F. R. Kaufman *Pediatr. Rev.* 18:383–392 (1997); and F. Ginsberg-Fellner *Pediatr. Rev.* 11:239–247 (1990)).

Various methods of accomplishing modulated in vivo drug delivery have been described in the literature and are currently in use or undergoing investigation. Mechanical pumps are one type of device that is commonly employed. Another method that has been examined is the use of ultrasound for "blasting off" a layer of material from a drug-containing polymer matrix to alter drug release. That method requires use of rigid, hydrophobic polymers that are generally incompatible with proteins and other hydrophilic macromolecular drugs. Other potential problems with the routine implementation of such ultrasound techniques may exist, as suggested by the widespread concern about the long term safety of repetitive exposure of body tissues to ultrasonic energy.

Other methods involving sequestration of various therapeutic agents by a polymer matrix material have been examined. For example, U.S. Pat. No. 5,986,043 (Hubbell et al.) describes certain biodegradable hydrogels as carriers for biologically active materials such as hormones, enzymes, antibiotics, antineoplastic agents, and cell suspensions. Delivery of the sequestered drug depends on the in vivo degradation characteristics of the carrier.

Certain temperature sensitive hydrophilic polymer gels, or hydrogels, have been described. When the temperature of the polymer is raised above its lower critical (or consolute) solution temperature (LCST), the hydrogel undergos a reversible phase transition that results in the collapse of the hydrogel structure (A. S. Hoffman et al. *J. Contr. Rel.* 4:213–222 (1986); and L. C. Dong et al. *J. Contr. Rel.* 4:223–227 (1986)). The hydrogel collapse forces soluble materials held within the hydrogel matrix to be expelled into the surrounding solution (R. Yoshida et al. *J. Biomater. Sci. Polymer Edn.* 6:585–598 (1994). An impediment in the development of temperature-sensitive materials into clinically useful modulated drug delivery devices has been the lack of satisfactory means for altering the temperature of the implanted device. Ideally, the temperature change should be localized to the device to avoid damage to surrounding tissue, but the temperature change also must be rapid in order to control the conformational changes in the polymer and the drug delivery profile. Other means of altering the temperature have been proposed and are being investigated, such as heating pads, non-targeted light and exothermic chemical reactions. Other proposed techniques for controlled drug release include the application of alternating magnetic fields to certain polymers with embedded magnetic particles to effect modulation of drug delivery. Iontopheresis has also been investigated.

None of the presently available methods or devices offer a satisfactory way of obtaining localized heating to accomplish controlled, thermally actuated drug release from an implantable device while adequately avoiding potential damage to the surrounding body tissue.

SUMMARY OF THE INVENTION

Methods, devices and compositions for the photothermally modulated release of a chemical from a release medium are provided by the present invention. In a particular embodiment, methods, devices and compositions for the in vivo localized, photothermally modulated release of a therapeutic agent, such as a drug, from an implanted medium are provided by the present invention. These methods, devices and compositions offer greater ability to localize heating and avoid potential damage to the surrounding tissue than is possible with existing methods and devices. The new composites, and their methods of use, are compatible with many types of therapeutic agents, including chemicals, drugs, proteins and oligonucleotides. The modulation is highly repeatable, allowing use of one device for many dosages.

One advantage of the present method and composite is the ability to locally change the temperature of a thermally responsive material by exposure to light targeted for absorption and conversion to heat by engineered nanostructures (metal nanoshells). This allows implantation of a drug delivery device with many dosages, and provides for external control over the dosage profiles by regulating exposure to an appropriate light source.

In accordance with the present invention, a composition for modulated in vivo drug delivery to a subject in need thereof is provided. In certain embodiments the composition comprises a plurality of heat generating particles. Each of these particles has a non-conducting core with an independently defined radius, a metal shell adhering to the core and also having an independently defined thickness. The terms "independently defined radius" and "independently defined thickness" mean that the desired thickness of each of the shell and core can be chosen and formed without dictating the thickness of the other. Each particle also includes a defined core radius:shell thickness ratio, and a defined wavelength absorbance maximum in the near-infrared range of the electromagnetic spectrum. In preferred embodiments, the shell and core are joined by a linker molecule. The composition may be in the form of a dry composite hydrogel, suitable for being rehydrated at a later time and loaded with a drug in aqueous solution. In certain embodiments the composite contains at least one therapeutic agent, such as a drug or a biologically active material, and a suitable medium, support or carrier in a hydrated form. The medium comprises a thermally responsive material in contact with the particles. The necessary thermal contact may be establishment of a polymer/particle interface, by chemical binding of the particle surface to the polymer, or the like. The therapeutic agent is reversibly contained in the composition when the temperature of the composition is at or below approximately normal body temperature of a subject, e.g., about 37° C. In some embodiments, the agent is reversibly released from the composition when the temperature is about 40° C. or more. In preferred embodiments, the medium contains a polymer hydrogel in which the thermally responsive material is substantially solid at normal body temperature of the subject (e.g., 37° C.) and undergoes a reversible phase transition at temperatures about 3 or more degrees C. above normal (e.g., 40° C.), and preferably between about 40–45° C. The thermally responsive material may comprise more than one polymer in some embodiments. The particles of the composition are of such design that they convert incident radiation into heat energy when they are irradiated by light of a defined wavelength.

Certain preferred embodiments of the particles of the invention comprise a gold sulfide core and a gold shell. In certain other embodiments the core comprises silicon dioxide and the shell comprises gold. In certain embodiments, optically tuned nanoshells are embedded within a polymer matrix. In certain embodiments, nanoshells are embedded in the surface of a N-isopropylacrylamide and acrylamide hydrogel. In certain other embodiments, the nanoshells and polymer together form microparticles, nanoparticles, or vesicles. In some embodiments the particle core is between about 1 nm up to slightly less than 5 $\mu$m in diameter, the shell is about 1–100 nm thick, and the particle has an absorbance maximum wavelength of about 300 nm to 20 $\mu$m, 600 nm to 10 $\mu$m preferably in the near-infrared range.

Another aspect of the present invention provides optically heatable particles suitable for use in the new compositions described above. The particles effectively convert incident electro-magnetic radiation into heat energy when they are irradiated. The conversion of incident electromagnetic radiation into heat energy is optimized when the incident radiation is at the defined wavelength at which the particles' absorbance is at its maximum.

Still another aspect of the invention provides a system for modulated in vivo delivery of a therapeutic agent. According to certain embodiments, the system comprises an implantable composition containing a plurality of photothermally responsive particles, as described above, at least one therapeutic agent, and a medium. The medium comprises a thermally responsive material in contact with the particles and is characterized as described above. The modulated in vivo delivery system may optionally include a biosensor system, for providing information about in vivo status to assist in making treatment decisions. If desired, the composition may be contained in an implantable porous or permeable device.

In still another aspect of the invention, a method of photothermally modulating in vivo delivery of a therapeutic agent is provided. According to certain embodiments, the method includes implanting into the body of a subject in need of treatment, a composition or a device containing a plurality of particles, at least one therapeutic agent, and a medium. The composition, which may be one of the above-described compositions, includes a thermally responsive material in contact with the particles. Preferably the material has a defined lower critical solution temperature that is slightly above the normal body temperature of the subject. The agent is substantially retained by the composition when the temperature of the composition is at about normal body temperature of the subject. At least a portion of the agent is substantially released from the composition into the body of the subject when the temperature of the composition, or a portion thereof, is raised to the lower critical solution temperature. The method includes applying electromagnetic radiation, preferably near-infrared, to the implanted composition or device from outside the body. The amount and duration of irradiation is sufficient to raise the temperature of the particles such that the composition, or a portion thereof, is raised to the lower critical solution temperature, causing release of the agent to commence. Application of the radiation in continued until a desired amount of the agent has been released from the composition into the body. After all or the desired of the agent has been delivered, the composition is allowed to return to normal body temperature, whereupon drug delivery is reduced or ceased, as desired. In some embodiments of the method, the irradiation is repeated at a later time, if multiple dosing is desired.

BRIEF DESCRIPTION OF THE DRAWINGS

For a detailed description of the preferred embodiment of the invention, reference will now be made to the accompanying drawings wherein.

DETAILED DESCRIPTION OF PREFERRED EMBODIMENTS

Figure 1:
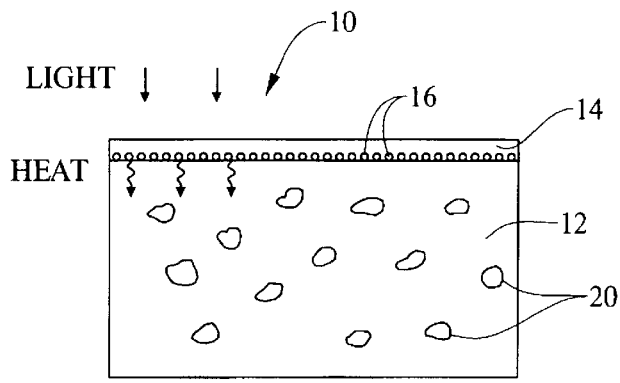
FIG. 1 is a schematic diagram of an optically heatable composition constructed in accordance with a first embodiment of the present invention, showing the composition in its pre-release state.

Composites of thermally sensitive hydrogels and optically active nanoparticles have been developed for use in photothermally modulated drug delivery. Copolymers of N-isopropylacrylamide (NIPAAm) and acrylamide (AAm) exhibit a lower critical solution temperature (LCST) that is slightly above body temperature. When the temperature of the copolymer exceeds the LCST, the hydrogel collapses, causing a rapid release or burst of any soluble material held within the hydrogel matrix.

In a preferred embodiment, gold-gold sulfide nanoshells, a new class of nanoparticles designed to strongly absorb certain wavelengths of light, have been incorporated into poly(NIPAAm-co-AAm) hydrogels for the purpose of initiating a temperature using the application of light to the composite. Light at wavelengths between 800 and 1200 nm is transmitted through tissue with relatively little attenuation, is absorbed by the nanoparticles, and is converted into heat. Heat generated in this manner causes collapse of the hydrogel in the vicinity causes significantly enhanced release of chemicals and proteins of varying molecular weight from the new composite hydrogels. Additionally, the ability of the present composite hydrogels to release multiple bursts of protein in response to repeated irradiation has been demonstrated.

In one embodiment of the present photothermally modulated chemical delivery system, near-infrared (near-IR) light is effectively converted to heat within a drug-containing thermally-reversible polymer matrix so as to alter the rate of drug delivery. Special metal coated particles ("nanoshells") are employed as heat transfer agents within the polymer matrix. Nanoshells have diameters ranging from a few nanometers up to about 5 microns and having defined wavelength absorbance maxima across the visible and infrared range of the electromagnetic spectrum. Gold nanoshells are a preferred class of optically active nanoparticles that consist of a thin layer of gold surrounding a dielectric core, such as gold sulfide (R. D. Averitt et al. *J. Opt. Soc. Am. B* 16:1824–1832 (1999); and R. D. Averitt et al. *Phys. Rev. Lett.* 78:4217–4220 (1997) or silicon dioxide (U.S. patent application Ser. No. 09/038,477).

According to one embodiment, nanoshells are preferably made by modifying the surface of a silica particle (the core) with aminopropyltriethoxysilane to add amine groups to the surface. These are then seeded with colloidal gold. Additional colloidal gold is added via chemical reduction in solution, to form the particle's gold shell layer. The wavelength of maximum optical absorption ($\lambda_{max}$) of a particle is determined by the ratio of the core radius to the shell thickness for a particle of given core and shell materials and particle diameter. Each of these variables (i.e., core radius and shell thickness) can be easily and independently controlled during fabrication of the nanoshells. Varying the shell thickness, core diameter, and the total nanoparticle diameter allows the optical properties of the nanoshells to be tuned over the visible and near-IR spectrum, as described and illustrated in more detail in U.S. patent application Ser. No. 09/038,377. By also varying the core and shell materials, which are preferably gold or silver over a silicon dioxide or $Au_2S$ core, the tunable range can be extended to cover most of the UV to near-infrared spectrum. Thus, the optical extinction profiles of the nanoshells can be modified so that the nanoshells optimally absorb light emitted from various lasers.

In the present case, in which photothermally controlled subcutaneous drug delivery was investigated, nanoshells were tuned to absorb near-IR light, particularly in a spectral range called the "water window." This refers to a gap in the absorption spectrum of tissue that exists between the absorption spectra of the chromophores (<800 nm) and that of water (>1200 nm) (C. R. Simpson et al. *Phys. Med. Biol.* 43:2465–2478 (1998)).

According to the present invention, a drug/polymer/nanoshell composite material incorporating these tuned nanoshells is implanted at the desired site in the body, such as subcutaneously. Light emitted at wavelengths between 800 and 1200 nm passes through tissue (C. R. Simpson et al. *Phys. Med. Biol.* 43:2465–2478 (1998), and is then absorbed by the tuned nanoshells that are embedded within the hydrogel. For example, near infrared light from an Nd:Yag laser, can be applied from outside the body. As the near-IR light is absorbed by the nanoshells, heat is generated and transferred to the polymer matrix nearby. As a result, the temperature of the polymer is increased above the polymer's lower critical solution temperature (LCST), causing a conformational change in the copolymer that leads to alterations in the release profile of the entrapped drug.

Temperature Sensitive Polymers

Temperature sensitive polymers, such as N-isopropylacrylamide and elastin peptide polymers, were examined as candidates for a modulated drug delivery application, since they are capable of repetitive changes in polymer conformation (and thus permeability and rate of drug delivery) in response to relatively small changes in temperature. Photothermally modulated drug delivery, wherein a device is implanted that allows the rate of drug delivery to be controlled by the application of electromagnetic energy to the device, is expected to be therapeutically beneficial in many cases, but especially so in insulin therapy. Near infrared light (800–1100 nm) passes through tissue with very little attenuation since there is very little absorption by the tissue. Thus, external access to an implanted device is possible and heating of the tissue surrounding the device is substantially avoided.

As stated above, N-isopropylacrylamide-co-acrylamide (NIPAAm-co-Aam) hydrogels are temperature-sensitive polymers whose lower critical solution temperatures (LCST) are only slightly above body temperature. When the temperature of the polymer is raised above its LCST, it undergoes a reversible phase transition, resulting in collapse of the NIPAAm-co-AAm hydrogel structure (A. S. Hoffman et al. *J. Contr. Rel.* 4:213–222 (1986); and L. C. Dong et al. *J. Contr. Rel.* 4:223–227 (1986). The collapse forces materials held within the hydrogel matrix to be expelled into the surrounding solution (R. Yoshida et al. *J. Biomater. Sci. Polymer Edn.* 6:585–598 (1994). Pure NIPAAm hydrogels form a thick skin on their surface when they collapse, however, which greatly reduces transport of materials out of the hydrogels after the skin is formed (R. Yoshida et al. *J. Biomater. Sci Polymer Edn.* 6:585–598 (1994). Additionally, the LCST of unmodified NIPAAm is 32° C., well below body temperature (J. H. Priest et al. *Reversible Polymer Gels and Related Systems* 350:255–264 (1987); and L. C. Dong et al. *Reversible Polymer Gels and Related Systems* 350:236–244 (1987)).

Copolymers formed of NIPAAm with the more hydrophilic AAm form a relatively thin surface layer, allowing soluble materials held within the hydrogel matrix to be more easily expelled into the surrounding solution during hydrogel collapse. NIPAAm-co-AAm hydrogels can have a LCST ranging from 32–65° C., depending on the amount of AAm included in the copolymer. A copolymer hydrogel consisting of 95% NIPAAm and 5% AAm has a LCST of approximately 40° C. (J. H. Priest, et al. *Reversible Polymer Gels and Related Systems* 350:255–264 (1987); and L. C. Dong et al. *Reversible Polymer Gels and Related Systems* 350:236–244 (1987). Hence, such a copolymer hydrogel is suitable for use in applications where it is desired to cause collapse of the hydrogel at temperatures only slightly above the normal core temperature of the human body.

Since it is not desirable to heat an implanted hydrogel directly, as this could cause thermal damage to the surrounding tissue, it is desirable to transfer energy to the hydrogel by some other means. IR light is one such means. NIPAAm-co-AAm hydrogels do not strongly absorb near IR light however. Thus, in order to achieve heating at the hydrogel with light that can pass harmlessly through surrounding tissue, light-absorbing nanoshells were embedded in the surface of a NIPAAm-co-AAm hydrogel. The extinction spectra of the composite over the near-IR spectrum is dictated by the nanoshells, while the phase transition characteristics of a NIPAAm-co-AAni copolymer with a LCST of approximately 40° C. are maintained in the composite.

Metal Nanoshells

As mentioned above, metal nanoshells are a new type of "nanoparticle" composed of a non-conducting, semiconductor or dielectric core coated with an ultrathin metallic layer. The diameter of a nanoshell particle can exceed the nanometer range, extending from about 1 nm to about 5 microns. As more fully described in co-pending U.S. patent application Ser. No. 09/038,377, metal nanoshells manifest unique physical properties. Specifically, metal nanoshells possess optical properties similar to metal colloids, i.e., a strong optical absorption and an extremely large and fast third-order nonlinear optical (NLO) polarizability associated with their plasmon resonance.

At resonance, dilute solutions of gold colloid possess some of the strongest electronic NLO susceptibilities of any known substance. (Hache, F. et al. *App. Phys.* 47:347–357 (1988)). Metal nanoshells exhibit similarly strong electronic NLO susceptibilities. However, unlike simple metal colloids which each have only a single resonance frequencies, the plasmon resonance frequency of metal nanoshells depends on the relative size of the nanoparticle core and the thickness of the metallic shell (Neeves, A. E. et al. *J. Opt. Soc. Am.* B6:787 (1989); and Kreibig, U. et al. Optical Properties of Metal Clusters, Springer, N.Y. (1995)). By adjusting the relative core and shell thickness, metal nanoshells can be fabricated that will absorb or scatter light at any wavelength across the entire visible and infrared range of the electromagnetic spectrum. The relative size or depth of the particle's constituent layers determines the wavelength of its absorption. Whether the particle absorbs or scatters incident radiation depends on the ratio of the particle diameter to the wavelength of the incident light.

For any given core and shell materials, the maximum absorbance of the particle depends upon the ratio of the thickness (i.e., radius) of the core to the thickness of the shell. Based on the core radius:shell thickness (core:shell) ratios that are achieved by the referenced synthesis method, nanoshells manifesting plasmon resonances extending from the visible region to approximately 5 $\mu$m in the infrared can be readily fabricated. By varying the conditions of the metal deposition reaction, the ratio of the thickness of the metal shell to the core radius can be varied in a predictable and controlled way. Accordingly, particles are constructed with core radius to shell thick ratios ranging from about 2–1000. This large ratio range coupled with control over the core size results in a particle that has a large, frequency-agile absorbance over most of the visible and infrared regions of the spectrum.

By comparison, the shifts induced in the plasmon resonance of gold colloid by adsorption of molecular species are quite small, typically 10 nm or less. (Kreibig (1995)) The nonlinear optical (NLO) properties of metal nanoshells or nanoshells-constituent materials can be resonantly enhanced by judicious placement of the plasmon resonance at or near the optical wavelengths of interest. The extremely agile "tunability" of the plasmon resonance is a property completely unique to metal nanoshells. In no other molecular or nanoparticle structure can the resonance of the optical absorption and NLO properties be systematically designed, much less so easily and over such an extremely wide range of wavelengths.

As described by Averitt, R. D. et al. (*Phys. Rev. Lett.* 78: 4217–4220 (1997)), the optical properties of certain metal nanoshells were investigated in detail by growing and studying gold-terminated gold sulfide nanoparticles. Gold-sulfide particle diameters are limited to sizes of approximately 40–45 nm with a thin gold shell (i.e., less than 5 nm) (H. S. Zhou et al. *Phys. Rev.,* 50:12052–12056 (1994). See, also Averitt et al. (1997) As described in Ser. No. 09/038,377 (also see Oldenburg, S. J. et al. *Chem. Phys. Lett* 288:243–247 (1998)), a more generalized method for the growth of a uniform metallic layer of nanometer scale thickness onto a dielectric core was developed. Briefly described, the process includes growing or obtaining dielectric or semiconductor nanoparticles dispersed in solution. Very small (i.e., 1–2 nm) metal "seed" colloid is tethered or attached to the surface of the nanoparticles, preferably via chemical or molecular linkages joining the shell layer to the dielectric core layer. Suitable linker molecules include any molecule that is capable of binding both the core and atoms, ions or molecules of the shell. Preferably, linker binding is covalent to both the shell and the inner layer, but binding may also be through ionic bonds, lone-pair interactions, hydrogen bonds, Van der Waals interaction or the like. The seed colloids cover the dielectric nanoparticle surfaces with a discontinuous metal colloid layer. Additional metal is then grown onto the "seed" metal colloid adsorbates by chemical reduction in solution. This approach has been successfully used to grow both gold and silver metallic shells onto silica nanoparticles.

Suitable metals for forming the shell or outer layer include the noble and coinage metals, but other electrically conductive metals may also be employed, the particular choice depending upon the desired use. Metals that are particularly well suited for use in shells include, but are not limited to, gold, silver, copper, platinum, palladium, lead, iron and the like. Gold and silver are preferred. Alloys or non-homogenous mixtures of such metals may also be used. The shell layer is preferably about 1 to 100 nm thick and coats the outer surface of the core uniformly, or it may partially coat the core with atomic or molecular clusters.

The core may have a spherical, cubical, cylindrical or other shape. Regardless of the geometry of the core, it is preferred that the particles be substantially homogeneous in size and shape, and preferably spherical. Preferably compositions comprising a plurality of metal nanoshells will contain particles of substantially uniform diameter ranging up to several microns, depending upon the desired absorbance maximum of the particles.

It is also preferred that the core or adjacent inner layer to the shell layer be nonconducting or dielectric. Suitable dielectric core materials include, but are not limited to, silicon dioxide, gold sulfide, titanium dioxide, polymethyl methacrylate (PMMA), polystyrene, and macromolecules such as dendrimers. The material of the nonconducting layer influences the properties of the particle, so the dielectric constant of the core material affects the absorbance characteristics of the particle. The core may be a mixed or layered combination of dielectric materials.

The particles employed in the present examples are two-layered, having a nonconducting core and a conducting outer layer or shell. If desired, an optically tuned multi-walled or multilayer nanoshell particle may be formed by alternating nonconducting and conducting layers. It is preferred that at least one shell layer readily conduct electricity, however, in some cases it is only necessary that one shell layer have a lower dielectric constant than the adjacent inner layer. The metal or metal-like shell layer is preferably the outermost layer. Additional layers may be attached to the adjacent layers using the methods described herein. The particles preferably have a homogeneous radius that can range from approximately 1 nanometers to several microns, depending upon the desired absorbance maximum of the embodiment.

An example of one embodiment of suitable nanoshells is as follows. Gold nanoshells with a 37 nm average diameter gold sulfide core and a gold shell average thickness of 4 nm were formed by combining 20 ml of 2 mM $HAuCl_4$ and 28 ml of 1 mM $Na_2S$. The progress of the reaction was monitored using an UV-visible spectrophotometer (U-2001, Hitachi Co., Tokyo) to observe the extinction spectrum of the solution from 400–1050 nm (Averitt et al. (1997) and Averitt et al. (1999)). As the nanoshells formed, the extinction spectra exhibited a peak that red-shifted into the IR, then halted and began to blue-shift into the visible spectrum. The peak narrowed and increased in magnitude as this occurred. 3.5 □l of mercaptoproprionic acid was added to halt this shift, by halting the growth of the gold shell, when the extinction peak reached the desired wavelength. For example, in one preparation where the wavelength of the laser to be used with the nanoshells was about 1064 nm, the growth of the gold shell was arrested when the extinction peak was centered around 1050 nm. The solution was then brought to pH 10.5 with 1 M NaOH, centrifuged at 3000 RPM for 20 minutes four times, and stored at 4° C. The size and polydispersity of the resulting nanoshells were determined by evaporating a drop of the nanoshell solution onto a carbon film on a copper grid and viewing the nanoshells via transmission electron microscopy (TEM, JEM-2010, JEOL, Peabody, Mass.). Other nanoshell preparations having a maximum absorbance wavelength of about 821 nm were prepared similarly. The maximum absorbance wavelength of the nanoshells is preferably within about 10–15 nm of the peak wavelength of the excitation laser to be employed. The gold/gold sulfide nanoshells made in this way could be formed with desired coating thicknesses and thus were tunable over a range of about 600–1,100 nm.

Other suitable metal nanoshells, such as gold/silicon dioxide can be fabricated as described in co-pending U.S. patent application Ser. No. 09/038,377 to provide photothermally sensitive particles for use in the preferred temperature-sensitive polymer composites for achieving photothermally controlled drug delivery.

Nanoshell-Composite Hydrogel Fabrication

Figure 2:
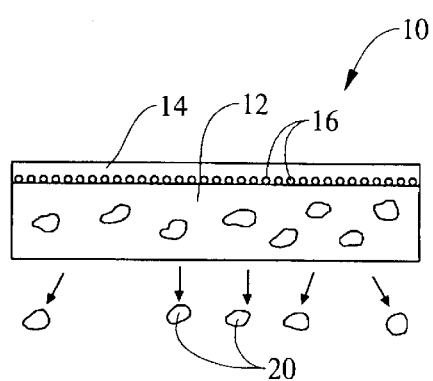
FIG. 2 is a schematic diagram of the composition of FIG. 1 showing it in its releasing state.

A nanoshell-composite hydrogel material is constructed in accordance with a preferred embodiment generally comprises a temperature sensitive copolymer and a quantity of nanoshells that have been designed to strongly absorb light at a predetermined wavelength. The nanoshells are embedded into one or more layers of the hydrogel material by mixing them with the liquid polymer precursors and then forming the polymer matrix. As shown schematically in FIG. 1, a nanoshell-containing hydrogel composite 10 constructed in accordance with a preferred embodiment of the present invention includes a hydrogel base layer 12, and a nanoshell containing heating layer 14. Base layer 12 contains particles of a chemical, drug or therapeutic agent 20 dispersed throughout and captured in the hydrogel matrix. If desired, the nanoshells 16 can be allowed to settle through the hydrogel in heating layer 14 before it cures, so that the nanoshells lie adjacent to base layer 12. When light at or near the resonance frequency of the nanoshells 16 is applied to the nanoshells, they become hot. The heat generated in this manner is transferred to base layer 12, which will collapse once it attains its collapse temperature. Collapse of base layer 12 causes release of the particles 20, as shown schematically in FIG. 2.

For example, one method for constructing a preferred composite is as follows. NIPAAm was mixed with acrylamide (to alter the lower critical solution temperature to be slightly above body temperature) and bis-acrylamide as a crosslinker. A free radical initiator was added, and the liquid was converted to a hydrogel. NIPAAm was obtained from Aldrich (Milwaukee, Wis.) and recrystallized in n-hexane.

AAm, N,N'-methylenebisacrylamide (MBAAm), ammonium persulfate (APS), N,N,N',N'-tetramethylethylenediamine (TEMED), HAuCl$_4$, Na$_2$S, mercaptoproprionic acid, and NaOH were used as received from Aldrich (Milwaukee, Wis.). In this study, hydrogels were constructed of two layers of 1.75 M poly(NIPAAm-co-AAm). The primary monomer solution was formed by placing a total of 15 ml of NIPAAm and AAm in a round-bottomed flask in a 95/5 molar ratio (NIPAAm-co-AAm). MBAAm was added as a crosslinker at a molar ratio of 1/750 (crosslinker/monomer). The flask was evacuated, and 50 $\mu$l of 1% APS solution (w/w) and 10 $\mu$l TEMED (6.6 $\mu$M) were added to initiate the redox reaction that forms the hydrogel. The hydrogel precursor solution was then poured into molds consisting of two glass slides separated by 1.5 mm Teflon spacers. After curing at 30° C. for 2 hours, the faceplate of the mold was removed, and the walls of the mold were extended by 1 mm. The faceplate was then replaced on the mold. An additional 10 ml of the monomer solution was prepared as described above, with the addition of 350 $\mu$l of the concentrated nanoshell suspension at the same time as the APS and TEMED. This secondary copolymer solution was then poured into the mold, over the initial hydrogel, and allowed to cure for 2 hours at 22° C. The resulting bilayer hydrogel was removed from the mold and allowed to swell in deionized water for 24 hours, after which it was cut into 1 cm diameter disks with a cork borer and dried overnight in a vacuum oven. Control bilayer hydrogels, lacking the nanoshells, were formed in the same manner but without the addition of the nanoshell suspension to the second monomer solution.

This bilayer structure, in which the nanoshells are concentrated in a thin surface layer, is preferred for this hydrogel system because the opaque thicker layer 12 scatters light appreciably and would make it difficult to achieve satisfactory energy transfer. To avoid this problem, the nanoshell-containing layer 12 was polymerized at a lower temperature and yielded a transparent, non-light scattering hydrogel that was chemically joined to the thicker layer. In its hydrated form, the bilayer hydrogel constructed in the foregoing manner demonstrated excellent handling qualities and suitability for use as an implantable device.

Alternatively, it may be desirable to prepare the drug-containing composite as an injectable composition for some applications. In these embodiments, the nanoshell-composite hydrogel can be formed as microparticles, nanoparticles, or vesicles, with the components arranged so as to allow effective absorption of incident radiation and effective heat transfer to the chemical-containing gel.

As described in more detail in the following examples, representative agents were loaded into these hydrogels by rehydration in the desired solutions. Alternatively, some agents may be combined with the hydrogel forming precursors without denaturation or loss of activity during the exothermic polymerization process.

Depending on the choice of metal for the shell of the embedded nanoshells, and the choice of the polymer for the hydrogel, in some instances there may be insufficient contact between the nanoshell surface and the polymer for adequate heat transfer. This may be overcome by chemically binding the two. For instance, a molecule with a thiol group and an acrylate group (e.g., Cys-PEG-acrylate) may be used. Binding or tethering of the nanoshells to the polymer may also be desirable in situations where the pore size of the hydrogel must be very large in order to release a large agent, such as an oligonucleotide, to avoid loss of small diameter nanoshells. In particular applications where it is desirable to have higher energy transfer from the nanoshell materials, it may be advantageous to alter the nanoshell structure, for example, by using double walled nanoshells. Fabrication of multiple walled, or layered, nanoshells can be carried out as described in U.S. patent application Ser. No. 08/038,477.

Still other variations or modifications of the above-described methods include embedding the nanoshells within a macroscopic matrix of thermally responsive material, particularly if spurious light scattering by the medium can be avoided. Alternatively, the light-absorbing nanoshells can be embedded or encased within microparticles of thermally responsive material. To prepare microparticulates, the thermally responsive polymer can be attached to the surface of individual nanoshells. As another alternative, the thermally responsive material may be used as the core of the nanoshell and the conducting shell applied as a coating to the outside of a thermally responsive material, in either a macroscopic or microscopic form.

Thermal Behavior of Exemplary Composites

Control and nanoshell-composite hydrogels (n=3 per group) were allowed to swell in Tris buffer (0.05 M, pH 7.4) for 24 hours at room temperature. The nanoshells used in this study comprised Au$_2$S cores and Au shells. The hydrogels were transferred to Tris buffer solutions held at 50° C. for 60 minutes, after which they were returned to a room temperature water bath. The hydrogels were weighed at set intervals throughout this procedure. Prior to weighing, they were dabbed with a damp paper towel to remove excess surface water. Additional sets of control and nanoshell-composite hydrogel disks were allowed to swell as previously described, then transferred to glass vials containing 500 □1 Tris buffer. Each vial was then irradiated along its vertical axis with a pulsed Nd:YAG laser (1064 nm, 164 mJ/pulse, 7 nsec pulse length, 10 Hz repetition rate, Surelite II, Continuum, Santa Clara, Calif.) such that the entire hydrogel was within the cross-sectional area of the beam. The thinner nanoshell embedded layer was positioned to face the laser beam. Alternatively, a continuous wave diode laser (821 or 832 nm, 700 mW, Coherent, Santa Clara, Calif.) was used to irradiate the composite-hydrogel disks. During 60 minutes of irradiation the hydrogels were weighed as described above at 10 minute intervals. The laser was turned off after 60 minutes, and the hydrogels were left at room temperature and weighed at 15 min. intervals for the next 30 minutes. The weight of the hydrogels was also recorded 24 hours after the start of the irradiation sequence. The % deswelling of control and nanoshell-containing hydrogels was determined. The degree of collapse and swelling of the hydrogels is represented by the deswelling ratio (DSR):

$$DSR = 100 \times (\text{Weight}(t) - \text{Weight}(t=0))$$

$$DSR = 100 \times \left( \frac{\text{Weight}(t)}{\text{Weight}(t=0)} \right)$$

Figure 3:
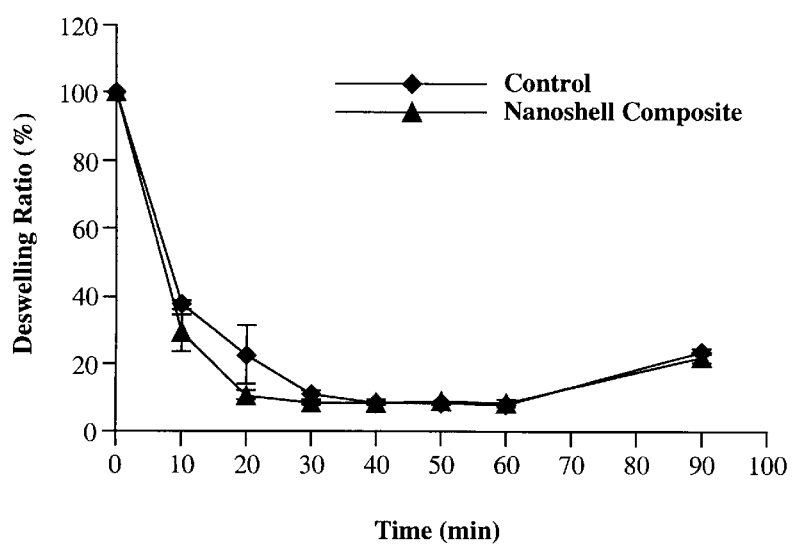
FIG. 3 is a graph showing the thermal behavior of NIPAAm-co-AAm hydrogels (diamond) and nanoshell-composite hydrogels (triangle) during immersion in 50° C. (0–60 min) and room temperature buffer (60–90 min). Data are mean ±SD.

The collapse of the nanoshell-composite hydrogels did not significantly deviate from that observed with NIPAAm-co-AAm control hydrogels when the method of heat transfer was direct heating, namely when the hydrogels were placed in a 50° C. water bath, as shown in FIG. 3. The collapse and swelling of NIPAAm-co-AAm hydrogels (diamond) and nanoshell-composite hydrogels (triangle) are shown during and after irradiation with a diode laser at 821 or 832 nm (800 mW) for 40 minutes. The deswelling ratio was tracked for an additional 30 minutes after irradiation ceased. Data are mean ±SD. Once the hydrogels were removed from the 50° C. buffer, both control and composite hydrogels swelled at the same rate. By 24 hr, all samples had returned to their equilibrium swelling state.

Figure 4A:
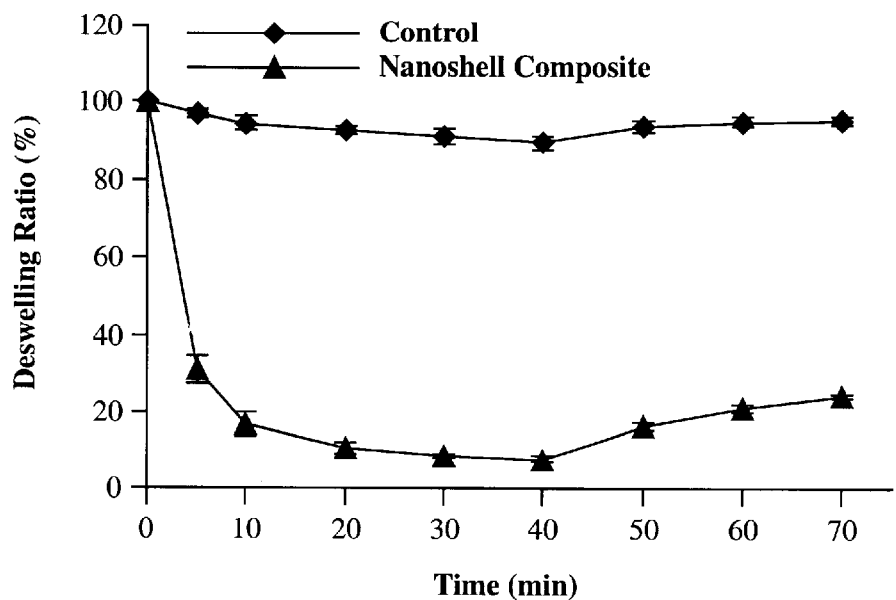
FIG. 4A is a graph showing the collapse and swelling of NIPAAm-co-AAm hydrogels (diamond) and nanoshell-composite hydrogels (triangle) during and after irradiation with diode laser at 821 nm (800 mW) for 40 minutes. The deswelling ratio was tracked for an additional 30 minutes after irradiation ceased. By 24 hr, all samples had returned to their equilibrium swelling state. Data are mean ±SD.
Figure 4B:
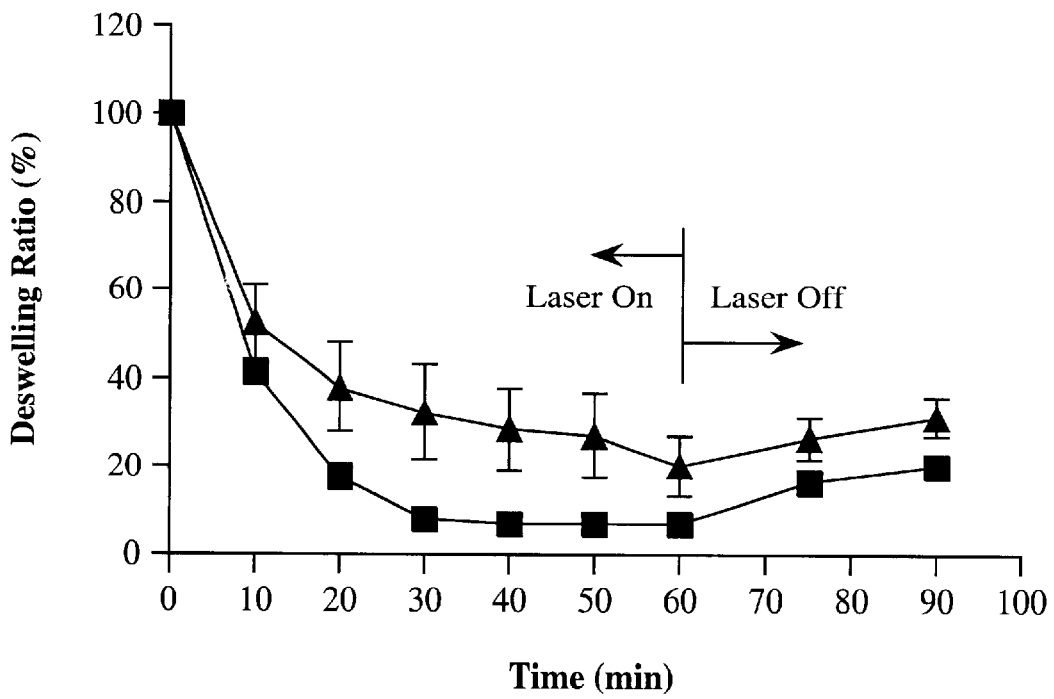
FIG. 4B is a graph showing the collapse and swelling of NIPAAm-co-AAm hydrogels (diamond) and nanoshell-composite hydrogels (square) during and after irradiation with an Nd:YAG laser at 1064 nm (164 mJ/pulse, 7 nsec pulse length, 10 Hz repetition rate) for one hour. The deswelling ratio was tracked for an additional 30 minutes after irradiation ceased. By 24 hr, all samples had returned to their equilibrium swelling state. Data are mean ±SEM.

The incorporation of the nanoshells into the composite hydrogels did, however, cause a marked difference in the rate of collapse when the method of heating was changed from immersion in warm buffer to near IR irradiation, as shown in FIG. 4A. The collapse and swelling of NIPAAm-co-AAm hydrogels (diamond) and nanoshell-composite hydrogels (triangle) during and after irradiation with a continuous diode laser (821 nm (800 mw) for 40 minutes are shown. FIG. 4B shows the results of a similar study in which the control and nanoshell-composite hydrogels were irradiated with a Nd:YAG laser (1064 nm (164 mJ/pulse, 7 nsec pulse length, 10 Hz repetition rate for one hour). It was observed that deswelling of the composite hydrogels was more pronounced than for the control hydrogels (without added nanoshells). In FIG. 4B the diamond shape represents NIPAAm-co-AAm hydrogels and the nanoshell-composite hydrogels are indicated by the squares.

Photothermally Modulated Drug Release

The drug release behavior of temperature-sensitive NIPAAm-co-AAm copolymers, with and without embedded nanoshells, was investigated to determine the suitability of these polymer-nanoshell composites for photothermally modulated drug delivery. The collapse of NIPAAm-co-AAm hydrogels due to immersion in a 50° C. water bath and laser irradiation at 1064 nm was measured in each case and compared to the collapse exhibited by nanoshell composite NIPAAm-co-AAm hydrogels under the same conditions. The amount of release induced by irradiation of the control and nanoshell composite hydrogels was compared for several model "drugs" of varying molecular weights. All data presented are the means of three samples with standard errors (SEM) shown in brackets. In these examples methylene blue was used to represent a low molecular weight "drug," and lysozyme, ovalbumin and BSA proteins represented higher molecular weight drugs or therapeutic agents.

EXAMPLE 1

Nanoshell-Mediated Release of Methylene Blue

Figure 5A:
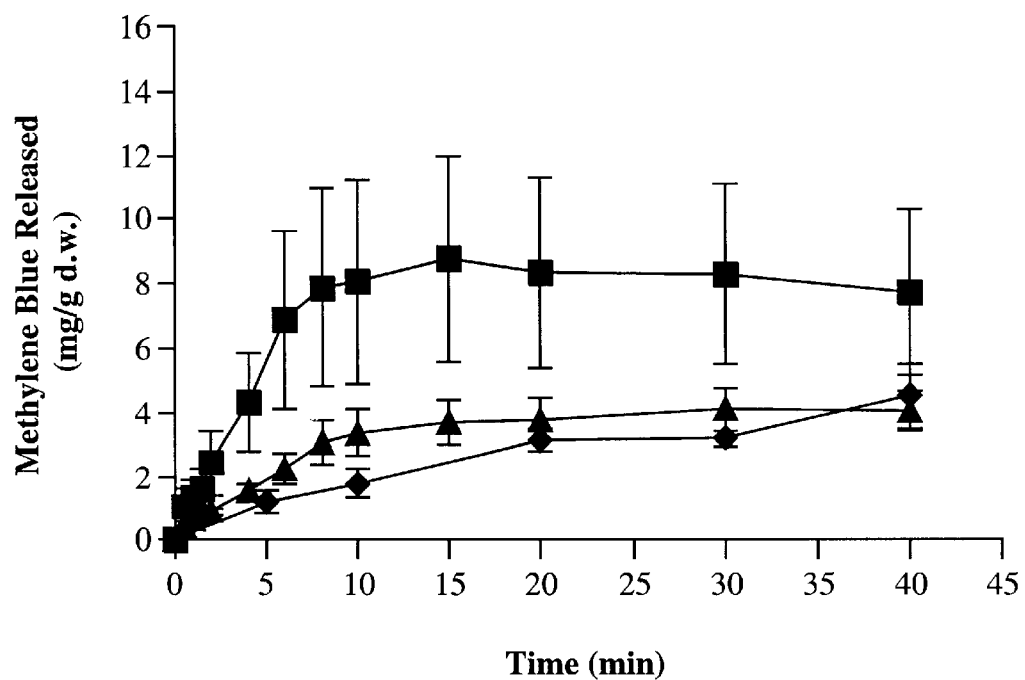
FIG. 5A is a graph showing the release of methylene blue from non-irradiated NIPAAm-co-AAm hydrogels (diamond), irradiated NIPAAm-co-AAm hydrogels (triangle), and irradiated nanoshell-composite hydrogels (square). Irradiation was at 1064 nm (164 mJ/pulse, 7 nsec pulse length, 10 Hz repetition rate) for 40 minutes. Data are mean ±SEM.

Dry nanoshell-composite hydrogels (n=3) were placed in a methylene blue dye solution (MW 374, 0.33 mg/ml in 0.05 M Tris buffer, pH 7.4) and allowed to swell for 48 hours at room temperature. After loading with methylene blue the ~1 cm diameter hydrogel disks were removed from the dye solution, quickly rinsed in fresh Tris buffer, and placed in a glass vial containing 2.4 ml of Tris buffer. The vial was then irradiated along its vertical axis with a pulsed Nd:YAG laser as described above. The hydrogels were irradiated for 40 min. Samples of the Tris buffer were removed from the vial at set intervals, and the absorbance at 663.5 nm was measured to determine the concentration of methylene blue in the release buffer. The amounts of methylene blue released after 0–40 minutes irradiation are shown in FIG. 5A. In the figure, results for the non-irradiated controls are represented by diamonds. The irradiated NIPAAm-co-AAm hydrogels are represented by triangles, and the irradiated nanoshell-composite hydrogels by the squares. Irradiation was at 1064 nm (164 mJ/pulse, 7 nsec pulse length, 10 Hz repetition rate) for 40 minutes. Data are mean ±SEM.

EXAMPLE 2

Nanoshell-Mediated Release of Ovalbumin

Figure 5B:
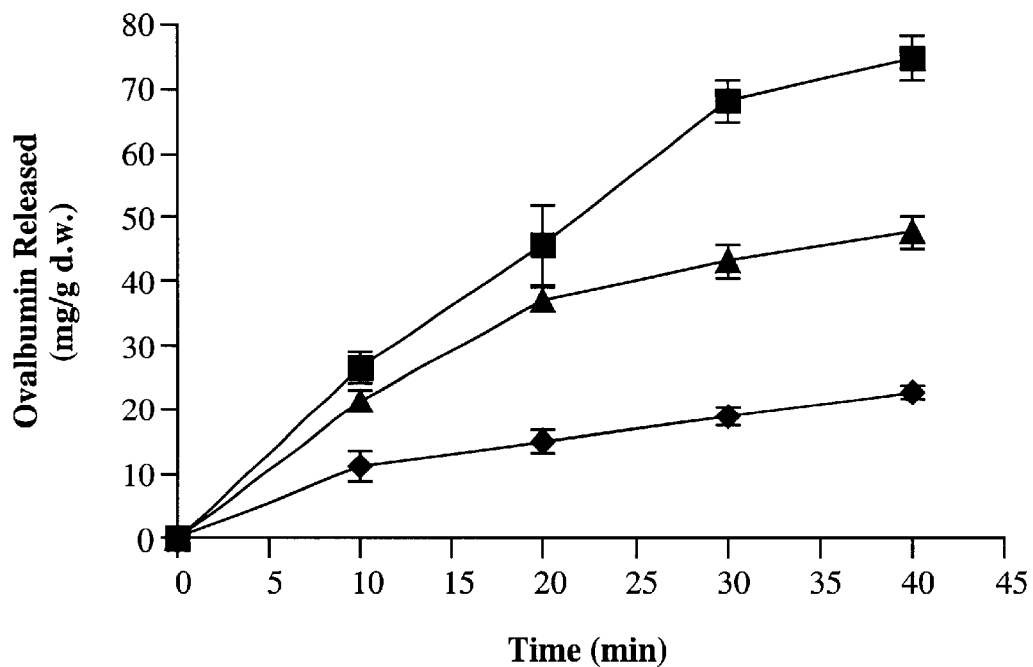
FIG. 5B is a graph showing the release of ovalbumin from non-irradiated NIPAAm-co-AAm hydrogels (diamond), irradiated NIPAAm-co-AAm hydrogels (triangle), and irradiated nanoshell-composite hydrogels (square). Irradiation was at 1064 nm (164 mJ/pulse, 7 nsec pulse length, 10 Hz repetition rate) for 40 minutes. Data are mean ±SEM.

Dry nanoshell-composite hydrogels (n=3 per group) were placed in a 10 mg/ml solutions of ovalbumin (MW 45,000) and allowed to swell for 48 hours at 4° C. The ovalbumin loaded hydrogels were then rinsed and irradiated as described above. The amounts of ovalbumin released were determined using a conventional bicinchoninic acid protein assay (Pierce, Rockford, Ill.). Controls consisted of NIPAAm-co-AAm hydrogels without nanoshells irradiated by the laser, as well as hydrogels not subjected to laser irradiation. FIG. 5B shows the release of ovalbumin from non-irradiated (diamond), irradiated NIPAAm-co-AAm hydrogels (triangle), and irradiated nanoshell-composite hydrogels (square). Irradiation was at 1064 nm (164 mJ/pulse, 7 nsec pulse length, 10 Hz repetition rate) for 40 minutes. Data are mean ±SEM.

EXAMPLE 3

Nanoshell-Mediated Release of Bovine Serum Albumin

Figure 5C:
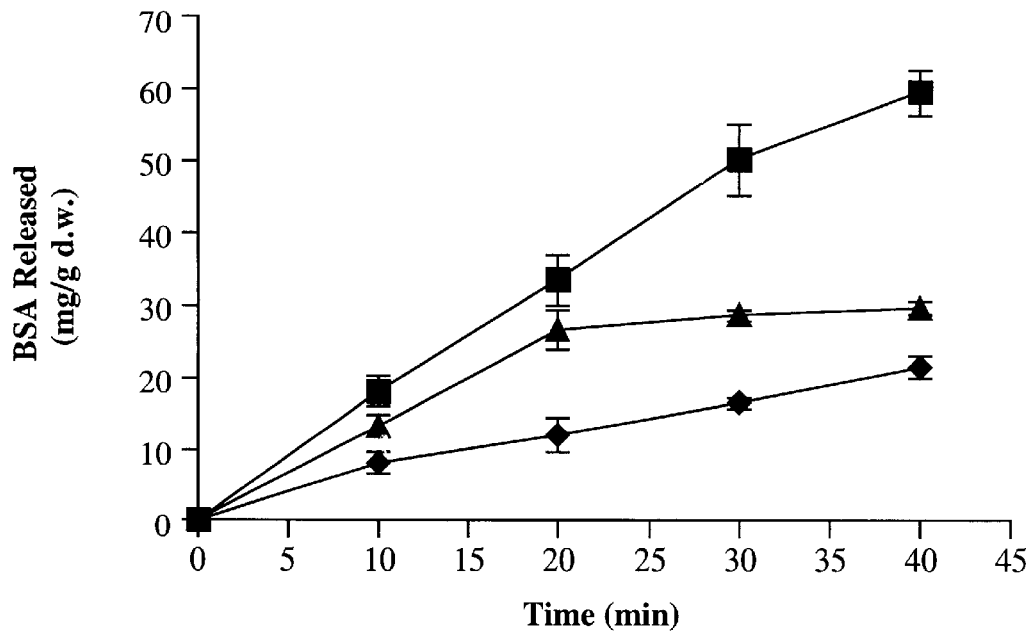
FIG. 5C is a graph showing release of bovine serum albumin (BSA) from non-irradiated NIPAAm-co-AAm hydrogels (square), irradiated NIPAAm-co-AAm hydrogels (diamond), and irradiated nanoshell-composite hydrogels (triangle). Irradiation was at 832 nm (700 mW) for 40 minutes. Data are mean ±SD.
Figure 5D:
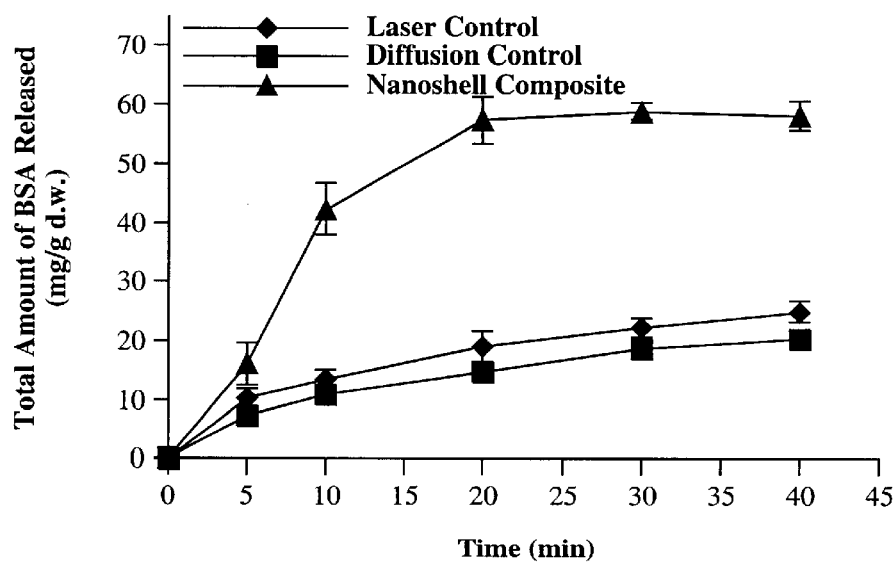
FIG. 5D is a graph showing release of BSA from non-irradiated NIPAAm-co-AAm hydrogels (square), irradiated NIPAAm-co-AAm hydrogels (diamond), and irradiated nanoshell-composite hydrogels (triangle). Irradiation was at 832 nm (700 mW) for 40 minutes. Data are mean ±SD.

Dry nanoshell-composite hydrogels (n–3 per group) were placed in 10 mg/ml solutions of bovine serum albumin (BSA, MW 66,000) and allowed to swell for 48 hours at 4° C. The BSA loaded hydrogels were then rinsed, irradiated for 5 minutes, allowed to swell for 20 minutes, then irradiated again for an additional 20 minutes to determine whether multiple bursts of release could be achieved with this system. The amount of BSA released was determined using the bicinchoninic acid protein assay. FIG. 5C shows the release of BSA from non-irradiated (diamond), irradiated NIPAAm-co-AAm hydrogels (triangle), and irradiated nanoshell-composite hydrogels (square). Irradiation was at 1064 nm (164 mJ/pulse, 7 nsec pulse length, 10 Hz repetition rate) for 40 minutes. Data are mean ±SEM. FIG. 5D shows the results obtained with a similar set of BSA-containing composite hydrogels that were irradiated at 821 nm (700 mW) for 40 minutes. The amount of BSA released from non-irradiated (square), irradiated NIPAAm-co-AAm hydrogels (diamond), and irradiated nanoshell-composite hydrogels (triangle) are shown.

The release of methylene blue, the low molecular weight model compound, from the nanoshell composite hydrogels was enhanced over that observed from laser-irradiated hydrogels without nanoshells, or non-irradiated hydrogels (FIG. 5A). Control hydrogels (without nanoshells) that had been loaded with ovalbumin and irradiated with the laser demonstrated some level of enhanced release when compared to non-irradiated hydrogels. However, the nanoshell composite hydrogels demonstrated a significant increase in the amount of ovalbumin released upon IR irradiation over both sets of control hydrogels (FIG. 5B). Similar results were obtained for the control and nanoshell composite hydrogels that were loaded with BSA (FIGS. 5C–D).

While the NIPAAm-co-AAm hydrogel does absorb a small amount of near-IR light and convert it to heat, resulting in a minor amount of hydrogel collapse, the nanoshells were specifically fabricated to strongly absorb light at this wavelength and convert it to heat, causing the local temperature of the nanoshell-composite hydrogels to increase rapidly upon near IR irradiation. The collapse of the hydrogel provides a convective force for the transport of the drug out of the hydrogel. The amount of drug released from the nanoshell-composite hydrogels is determined by the relative strengths of the diffusive and convective driving forces. The pore size and tortuosity of the hydrogel did not provide a large barrier to the diffusion of methylene blue. As a result, diffusion was the primary driving force for drug release and accounts for the small difference between the release of methylene blue in control and in nanoshell-composite hydrogels. The pore size of the hydrogel provided a greater hindrance to larger molecules like the proteins examined in this study, causing the convective force to be more predominant. As a consequence, convective transport became the dominant mechanism for drug release, causing the significant increase in the amount of ovalbumin and BSA released during laser irradiation, as shown in FIGS. 3B–C. and a greater difference between the composite samples and the controls

EXAMPLE 4

Repetitive Release of Bovine Serum Albumin

Figure 6A:
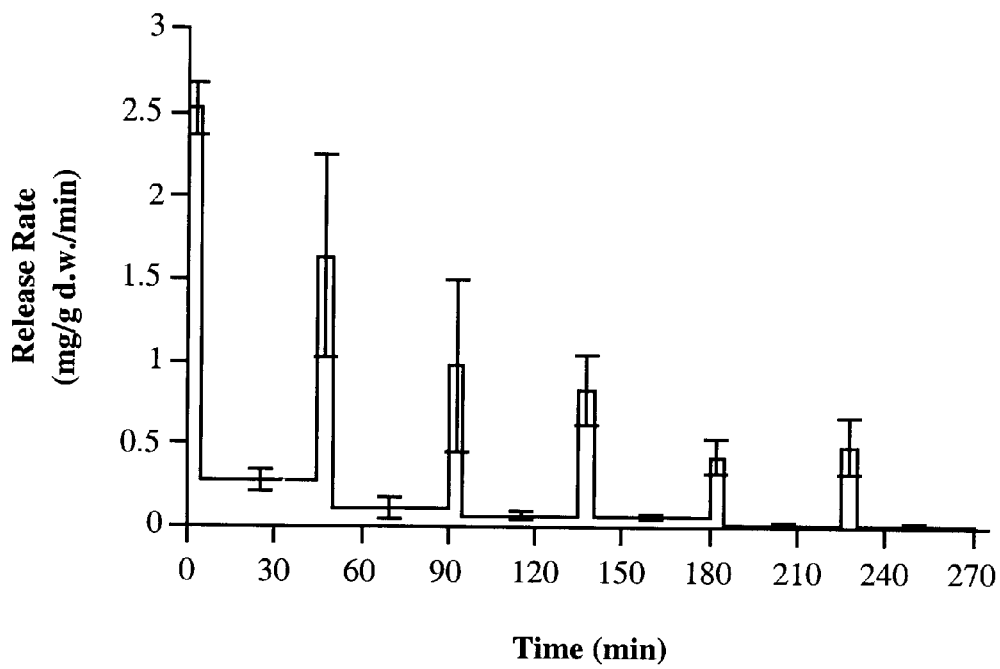
FIG. 6A is a graph showing release of BSA from nanoshell-composite hydrogels in response to sequential irradiation at 832 nm (800 mW). Data are mean ±SEM.
Figure 6B:
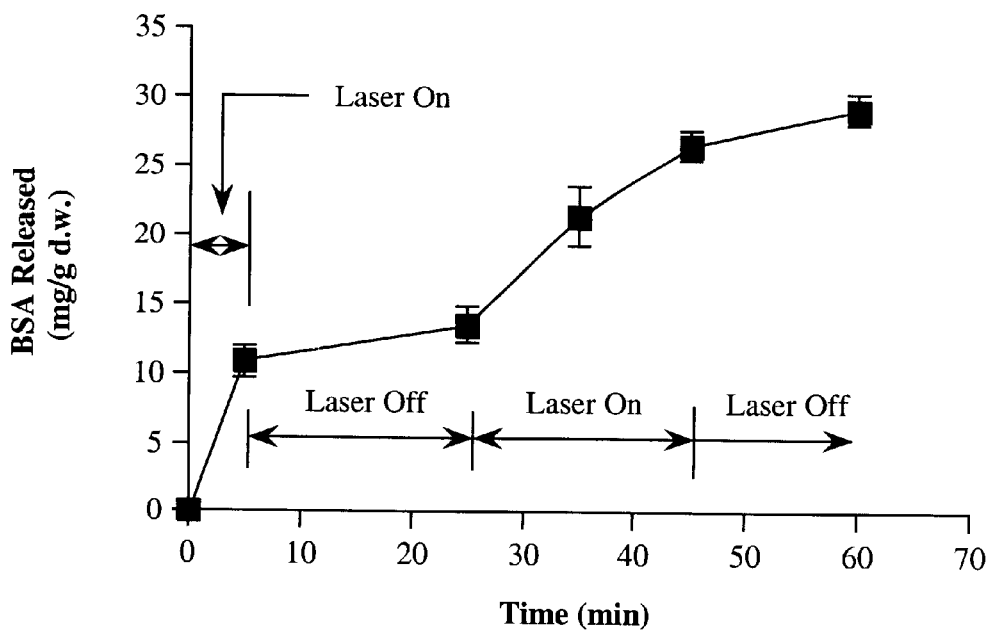
FIG. 6B is a graph showing the release of BSA from nanoshell-composite hydrogels in response to sequential irradiation at 1064 nm (164 mJ/pulse, 7 nsec pulse length, 10 Hz repetition rate). Irradiation was during the 0–5 minute period and the 25–35 minute period. Data are mean ±SEM.

If all of the drug or therapeutic agent is not released during the initial irradiation sequence, additional bursts of release of the drug can be elicited by subsequent irradiation, as shown in FIGS. 6A–B. Once the laser irradiation is stopped, the driving force for the convective transport of material out of the hydrogel matrix is removed. During this time, the drug release is driven by diffusion, and the amount released is much less than that generated by irradiation, particularly for larger drug molecules. The hydrogel will begin to swell as soon as the laser is turned off, returning to its equilibrium state. A second irradiation sequence delivered at this time will cause the hydrogel to collapse again, resulting in another burst of release of the drug molecule. This pattern of release was demonstrated for BSA.

A set of composite hydrogels were prepared as described in Example 3, however the control and BSA loaded composites were instead subjected to intermittent irradiation. In this case, corresponding multiple "bursts" of release of BSA from nanoshell composite hydrogels were obtained upon periodic irradiation. FIG. 6A shows pulsed release of BSA from nanoshell-composite hydrogels in response to sequential irradiation at 821 nm (800 mW) by a continuous diode laser. Data are mean ±SEM. FIG. 6B shows repeated release of BSA obtained at 1064 nm with a pulsed Nd:YAG laser (164 mJ/pulse, 7 nsec pulse length, 10 Hz repetition rate). As shown in FIG. 6B, the composites were irradiated during the 0–5 minute interval and the 25–35 minute interval. An increase in the rate of BSA release was observed when the laser was turned on, then the rate of release returned to a baseline level once the irradiation had ceased. A second application of laser irradiation resulted in another period of high BSA release followed by a return to a baseline level when the laser was turned off.

It has been observed that, at least in some instances, photothermal heating of a nanoshell-composite hydrogel sufficient to release a protein contained therein can be achieved without denaturing or inactivating the released protein.

Model for in vivo Triggering of Drug Release

Figure 7:
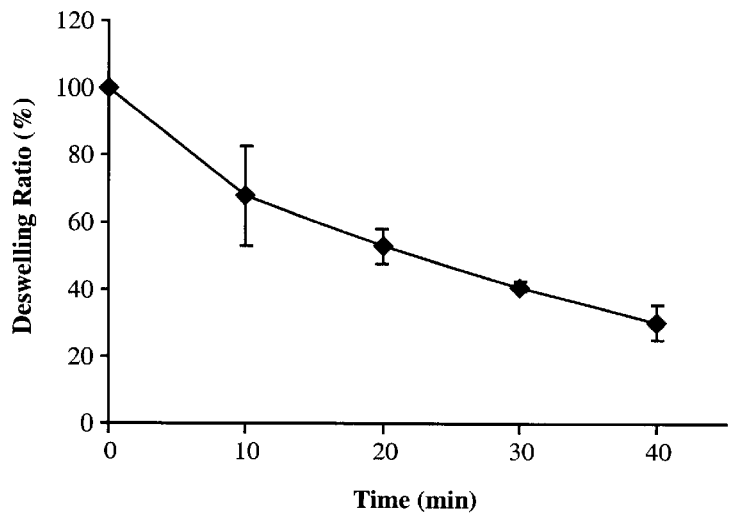
FIG. 7 is a graph showing collapse of nanoshell-composite hydrogels in response to irradiation through skin at 821 nm (1.5 W) for 40 min. Data are mean ±SD.
Figure 8:
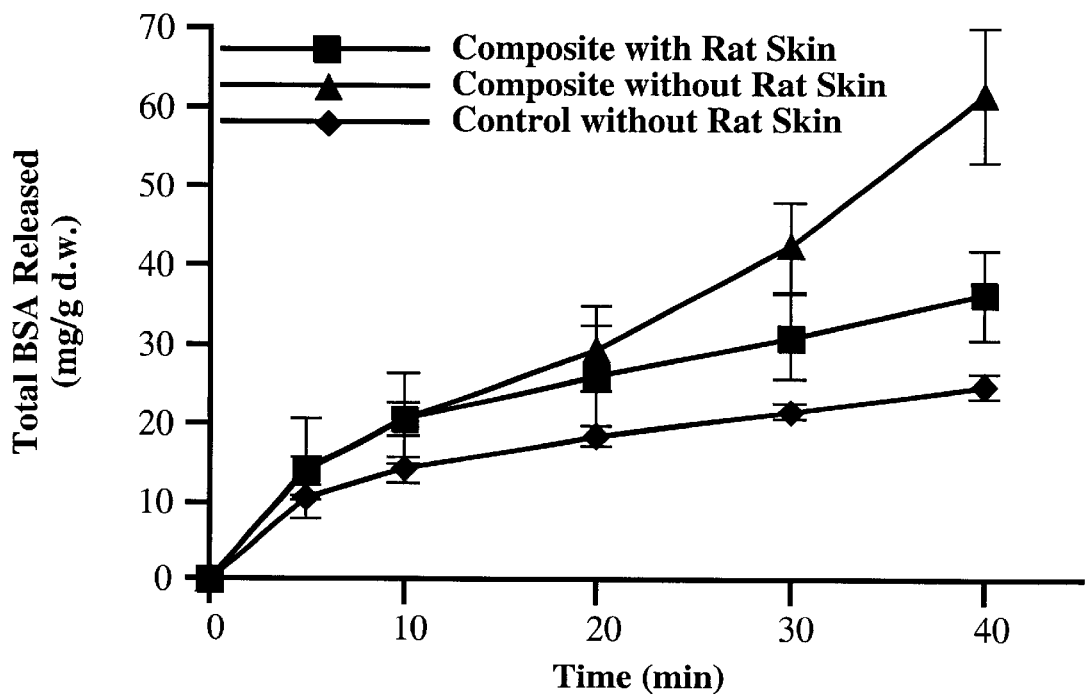
FIG. 8 is a graph showing release of BSA from nanoshell-composite hydrogels (square) that were irradiated through skin at 821 nm (1.5 W) for 40 min. Controls are identical nanoshell-composite hydrogels that were irradiated without passing the radiation through skin (triangle), and irradiated NIPAAm-co-AAm hydrogels without any rat skin present (diamond). Data are mean ±SD.

The triggering of a significant degree of collapse with near-infrared irradiation after light passage through skin and absorption by the nanoshell/hydrogel composite was demonstrated. A set of nanoshell-composite hydrogels were prepared and treated as described above, however, prior to irradiation a section of rat skin was placed above the vial containing the hydrogel to simulate an in vivo situation. The rat skin was obtained from a hooded Long-Evans rat immediately after sacrifice, and placed in a glycerol bath for 3 hours. The skin section was taken from the bath and the excess glycerol was removed with a paper towel. The section was then clamped into place above the glass vial, between the hydrogel and the fiber tip of the laser. The hydrogels were subsequently irradiated through the skin with the continuous diode laser (821 nm, 1.5 W) for a period of 40 minutes. The hydrogels were weighed at 10, 20, 30, and 40 minutes during the irradiation sequence. FIG. 7A shows collapse of nanoshell-composite hydrogels in response to irradiation through skin at 821 nm (1.5 W) employing a continuous diode laser. Data are mean ±SD. FIG. 8 shows the results obtained when BSA was included in the nanoshell composite hydrogel, as described in Example 3, and the composite was irradiated through rat skin under the same conditions. In FIG. 8, the irradiated nanoshell-composite hydrogels are indicated by squares. For comparison, the release of BSA from irradiated nanoshell-composite hydrogels (triangle) and irradiated NIPAAm-co-AAm hydrogels (diamond) without the overlying skin section are also shown. Irradiation was at 821 nm (1.5 W for 40 min.) using a continuous diode laser. Data are mean ±SD. No damage was apparent in the skin samples after the 40 minute irradiation periods.

Near IR light in controlled doses is generally considered to be safe for repeated exposure. An example of such an application is optical coherence tomography (OCT), a process in which the reflections of a near IR laser source are used to image tissues that lie beneath the skin (D. Huang et al. *Science* 254:1178–1181 (1991)). Lankenau et al. demonstrated the ability of OCT to image malignant melanomas in vivo without causing harm to the surrounding tissue (E. Lankenau et al. SPIE 2981:78–83 (1997)). Another field in which low power near IR irradiation has been successfully used is photodynamic therapy (PDT). PDT covers a large range of treatments in which a photosensitizer is introduced into the tissue of interest, then irradiated to induce an excited state in the photosensitizer (A. M. R. Fisher et al. *Lasers in Surgery and Medicine* 17:2–31 (1995)). Excitation to a singlet state results in fluorescence as the photosensitizer decays to its ground state. This technique has been used to image tumors in murine models (R. Weissleder et al. *Nature Biotechnology* 17:375–378 (1999)). Alternatively, when the photosensitizer is in a triplet excited state, this causes the formation of singlet oxygen, a cytotoxic substance. This second pathway has been used to selectively kill malignant tumor cells without damaging the surrounding cells (Fisher et al. (1995)).

The surface that the gold coated nanoshells present to the environment is a contiguous layer of gold. Gold is an essentially bioinert material and has found use in fields ranging from dental surgery to arthritis treatments (B. Merchant *Biologicals* 26:49–59 (1998); and P. O. Glantz *J. Biol. Buccale* 12:3–16 (1998)). In fact, it has been used as a reference material for evaluating the biocompatibility of less inert materials (C. Eriksson et al. *J. Biomed. Mater. Res.* 37:130–136 (1997). Thus, the gold shell surrounding the nanoshell core is not likely to induce an adverse biological reaction if the nanoshells become separated from the body of the hydrogel.

A variety of thermally responsive materials may be utilized for the drug delivery matrix. Poly-N-isopropylaerylamide (NIPAAm) and acrylamide are examples of suitable materials. Preferably the polymers are not biodegradable, however, as that might adversely effect the drug delivery capability. The composite, or device containing the composite, can be removed after depletion of the drug supply, which may be as long as several years after implantation.

These data indicate the feasibility of an implantable drug delivery system based on the conversion of energy from light to heat. It is expected that a drug release profile similar to those shown in FIGS. 4A–B will be useful in various therapies, including insulin therapy, as well as other applications, where controlled pulsatile release of a drug is necessary. In some therapeutic regimes it would be advantageous to employ this system in conjunction with a biosensing system such as that described in concurrently filed U.S. patent application Ser. No. 09/616,154. For example, after sensing an elevated glucose condition in the body of a diabetic patient via a biosensor implant, the near-IR modulated drug delivery system could be actuated to deliver the required dose of insulin.

While the preferred embodiments of the present invention have been set forth herein in terms of in vivo release of drugs or other chemicals, it is contemplated that the present optically heatable compositions have utility and can be used to advantage in many other applications. For example, in industrial applications, it may be desirable to release various chemicals, dyes, or other agents in response to an outside stimulus such as incident radiation. Likewise, in agricultural applications, it may be desirable to release a pesticide, herbicide, fertilizer, or other active agent in response to a stimulus in the form of incident radiation. Similarly, the present composites can be used in nanoscale assays and in certain control devices, where minute amounts of chemicals need to be introduced at various times. In each of these cases, the ability of the present composites to transform incident electromagnetic radiation into heat that in turn causes the release of the desired agent makes the present composites suitable for such use.

Similarly, while preferred embodiments containing particular nanoshells as the photothermal, or optically heatable, particles are discussed above, it is contemplated that other optically heatable particles can also be used, including colloidal metals, organic particles such as carbon black, metal oxides, and other particles that are efficient transformers of optical energy into heat.

While the preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. For example, although a preferred use of the new composites is for photothermally modulated in vivo drug release, one can readily appreciate that similar nanoshell-based composites could find use in a variety of industrial applications where externally controlled thermal release of a substance from a temperature sensitive polymer matrix is desired. Accordingly, the scope of protection is not limited by the description set out above, but is only limited by the claims which follow, that scope including all equivalents of the subject matter of the claims. The disclosures of all patents, patent documents, and publications cited herein are incorporated by reference to the extent that they describe pertinent materials or methods not explicitly set forth herein.

We claim:

1. A temperature-sensitive composition, comprising:
   a medium comprising a thermally responsive material; and
   a plurality of optically heatable particles capable of converting incident radiation into heat energy when said particles are irradiated with electromagnetic radiation; wherein said optically heatable particles are in thermal contact with said thermally responsive material, such that exposure of said optically heatable particles to said incident radiation radiation results in a temperature change in said thermally responsive polymer.

2. The composition of claim 1 wherein said particles each comprise:
   a non-conducting core,
   a metal shell adhering to said core and,
   a defined core radius:shell thickness ratio,
   optionally, a molecular linkage between said shell and said core, and
   said particles having a defined wavelength absorbance maximum when said particle is irradiated with said electromagnetic radiation.

3. The composition of claim 2 wherein said core has an independently defined diameter and said shell has an independently defined thickness.

4. The composition of claim 2 wherein said core is between about 1 nm and 5 μm in diameter, said shell is about 1–100 nm thick, and said particle has an absorbance maximum wavelength of about 600 nm to 10 μm.

5. The composition of claim 1 wherein said particles have a wavelength absorbance maximum between about 300 nm and about 20 μm.

6. The composition of claim 1 wherein said thermally responsive material comprises at least one polymer.

7. The composition of claim 6 wherein said at least one polymer is a copolymer of N-isopropylacrylamide and acrylamide.

8. The composition of claim 1 wherein said thermally responsive material is a hydrogel.

9. The composition of claim 1 wherein said medium comprises at least two layers.

10. The composition of claim 9 wherein said particles are embedded in at least one said layer.

11. The composition of claim 1 wherein said defined wavelength absorbance maximum of said particles is in the near-infrared range of the electromagnetic spectrum.

12. The composition of claim 1 wherein said particles and said thermally responsive material together form microparticulates.

13. The composition of claim 1 in the form of a desiccated polymer-particle composite capable of forming a hydrogel.

14. The composition of claim 1 further comprising at least one chemical agent releasably contained in said medium such that when the temperature of said medium or portion thereof is at a first temperature said agent is retained, and when said medium or a portion thereof is at a second temperature higher than said first temperature, at least a portion of said agent is released from said medium.

15. The composition of claim 14 wherein said thermally responsive material is substantially solid at said first temperature and undergoes a reversible phase transition above said second temperature.

16. A temperature-sensitive composition, comprising:
   a medium comprising a hydrogel; and
   a plurality of optically heatable particles, each comprising:
   a non-conducting core,
   a metal shell adhering to said core and,
   a defined core radius:shell thickness ratio,
   optionally, a molecular linkage between said shell and said core, and
   said particles having a defined wavelength absorbance maximum when said particle is irradiated with electromagnetic radiation,
   wherein said optically heatable particles are in thermal contact with said hydrogel, such that exposure of said optically heatable particles to said incident radiation radiation results in a temperature change in said thermally responsive polymer.

17. The composition of claim 16 wherein said particles have a wavelength absorbance maximum between about 300 nm and about 20 μm.

18. The composition of claim 16 wherein said particles and said hydrogel together form microparticulates.

19. The composition of claim 16 further comprising at least one chemical agent releasably contained in said medium such that when the temperature of said medium or portion thereof is at a first temperature said agent is retained, and when said medium or a portion thereof is at a second temperature higher than said first temperature, at least a portion of said agent is released from said medium.

20. The composition of claim 16 wherein said hydrogel is substantially solid at said first temperature and undergoes a reversible phase transition above said second temperature.

* * * * *